United States Patent
Raslambekov

(10) Patent No.: US 12,285,310 B2
(45) Date of Patent: *Apr. 29, 2025

(54) METHODS AND SYSTEMS FOR DETERMINING OCCLUSAL CONTACTS BETWEEN TEETH OF A SUBJECT

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 382 days.

This patent is subject to a terminal disclaimer.

(21) Appl. No.: 17/543,186

(22) Filed: Dec. 6, 2021

(65) Prior Publication Data

US 2022/0361983 A1 Nov. 17, 2022

Related U.S. Application Data

(63) Continuation of application No. 17/319,288, filed on May 13, 2021, now Pat. No. 11,191,619.

(51) Int. Cl.
| | |
|---|---|
| *A61C 7/00* | (2006.01) |
| *A61C 19/05* | (2006.01) |
| *G06F 30/12* | (2020.01) |
| *G16H 30/40* | (2018.01) |
| *A61C 7/08* | (2006.01) |
| *A61C 9/00* | (2006.01) |

(52) U.S. Cl.
CPC ............ *A61C 7/002* (2013.01); *A61C 19/05* (2013.01); *G06F 30/12* (2020.01); *G16H 30/40* (2018.01); *A61C 7/08* (2013.01); *A61C 9/0046* (2013.01)

(58) Field of Classification Search
CPC .......... A61C 7/002; A61C 19/05; A61C 7/08; A61C 9/0046; G61H 30/40; G61H 30/12
See application file for complete search history.

(56) References Cited

U.S. PATENT DOCUMENTS

| | | | |
|---|---|---|---|
| 6,152,731 | A | 11/2000 | Jordan et al. |
| 6,334,853 | B1 | 1/2002 | Kopelman et al. |
| 7,160,110 | B2 | 1/2007 | Imgrund et al. |
| 7,716,024 | B2 | 5/2010 | Hultgren et al. |

(Continued)

FOREIGN PATENT DOCUMENTS

| | | |
|---|---|---|
| WO | 2020037598 A1 | 2/2020 |
| WO | 2020181973 A1 | 9/2020 |

OTHER PUBLICATIONS

U.S. Appl. No. 17/143,074, filed Jan. 6, 2021.

*Primary Examiner* — Nicholas D Lucchesi
(74) *Attorney, Agent, or Firm* — BCF LLP

(57) ABSTRACT

A method and a system for determining occlusal contacts between lower teeth and upper teeth of a subject are provided. The method comprises: receiving a 3D model including a first portion and a second portion including points respectively representative of the lower teeth and the upper teeth; determining an occlusal plane associated with the second portion of the 3D model; determining, from each point of the first portion, respective distance values to the occlusal plane; and identifying, within the points of the first portion, based on the respective distance values, using a voxel grid, a set of occlusal points representative of at least some of the occlusal contacts between the lower teeth and the upper teeth.

20 Claims, 8 Drawing Sheets

(56) References Cited

U.S. PATENT DOCUMENTS

| | | |
|---|---|---|
| 8,494,241 B2 | 7/2013 | Kadobayashi et al. |
| 8,585,400 B2 | 11/2013 | Hultgren et al. |
| 8,587,582 B2 | 11/2013 | Matov et al. |
| 9,226,806 B2 | 1/2016 | Manai et al. |
| 9,549,788 B2 | 1/2017 | Inglese et al. |
| 9,848,958 B2 | 12/2017 | Matov et al. |
| 10,695,146 B1 | 6/2020 | Raslambekov |
| 10,695,147 B1 | 6/2020 | Raslambekov |
| 10,898,298 B1 | 1/2021 | Raslambekov |
| 10,993,782 B1 | 5/2021 | Raslambekov |
| 11,364,103 B1* | 6/2022 | Raslambekov ......... G06T 19/20 |
| 2002/0006217 A1* | 1/2002 | Rubbert ................. A61C 7/146 382/154 |
| 2002/0094509 A1 | 7/2002 | Durbin et al. |
| 2012/0236135 A1 | 9/2012 | Daniel et al. |
| 2014/0172377 A1 | 6/2014 | Taubin et al. |
| 2016/0271379 A1 | 9/2016 | Pouliot et al. |
| 2018/0235437 A1 | 8/2018 | Ozerov et al. |
| 2018/0333231 A1* | 11/2018 | Somasundaram ...... G06T 19/20 |
| 2019/0066537 A1 | 2/2019 | Van Den Braber et al. |
| 2019/0216580 A1 | 7/2019 | Fisker et al. |
| 2019/0259202 A1 | 8/2019 | Taubin et al. |
| 2019/0290408 A1* | 9/2019 | Fisker .................... A61C 11/00 |
| 2019/0374318 A1 | 12/2019 | Jesenko |
| 2020/0022789 A1 | 1/2020 | Jesenko |
| 2020/0037848 A1 | 2/2020 | Ozerov et al. |
| 2020/0265653 A1 | 8/2020 | Hawkins et al. |
| 2021/0174585 A1 | 6/2021 | Huber et al. |

\* cited by examiner

METHODS AND SYSTEMS FOR DETERMINING OCCLUSAL CONTACTS BETWEEN TEETH OF A SUBJECT

CROSS-REFERENCE

The present application is a Continuation of U.S. patent application Ser. No. 17/319,288 filed on May 13, 2021, content of which is incorporated herein by reference in its entirety.

FIELD

The present technology relates to systems and methods useful for determining an orthodontic treatment for a subject; and more specifically, although not exclusively, to determining occlusal contacts between subject's teeth.

BACKGROUND

In orthodontics, treatments for achieving alignment of malposed teeth in a subject may include both surgical and non-surgical approaches aimed at causing subject's teeth to move to a desired position thereof, such as that associated with their alignment. Another purpose of the orthodontic treatment may be attaining a state of normal occlusion between upper teeth and lower teeth of the subject—that is a state where the upper teeth and the lower teeth of the subject are positioned in a predetermined (can also be referred to as "standard") mutual spatial relationship when a mouth of the subject is closed. For example, the normal occlusion may occur when certain cusps of the upper teeth are received in grooves of the lower teeth of the subject. Another indicator of the normal occlusion can be matching respective midlines of the upper teeth and the lower teeth of the subjects.

Non-surgical interventions may include, for example, applying dental appliances, such as orthodontic aligners, to the subject's teeth. Orthodontic aligners are typically worn over teeth of an arch form in order to exert a force to the subject's teeth to move the teeth to a desired position, such as to align malocclusions. Surgical approaches include various surgical corrections of the subject's skull, such as a maxillary impaction surgery and others.

At certain stages of the orthodontic treatment, it may be practical to determine occlusal contacts between the subject's teeth, that is, contacts between occlusal surfaces of opposing ones of the lower teeth and the upper teeth of the subject.

For example, the occlusal contacts may be determined at the stage of planning the orthodontic treatment to model tooth movements. More specifically, modelling movements of a given tooth may include modelling at least one of (1) movements of the given tooth within teeth (such as the lower teeth) of an associated arch form and (2) movements of the given tooth relative to teeth (such as the upper teeth) of an opposing arch form. In this regard, the occlusal contacts may be determined to ensure that the subject's teeth would not be damaged under forces exerted by thus produced one or more dental appliances.

In another example, the occlusal contacts may be determined to observe the progress of the orthodontic treatment and to monitor whether the subject's teeth attain the state of normal occlusion therebetween.

In other words, the occlusal contacts may be determined for modelling positions of the lower teeth relative to the upper teeth in the course of the orthodontic treatment. For example, mesh 3D representations of surfaces of the subject's arch forms can be generated, and the occlusal contacts may be determined by determining distances between vertices of the mesh 3D representations representative of occlusal surfaces of the upper teeth and lower teeth.

Further, the determined distances may be mapped onto at least one of the mesh 3D representations of the subject's teeth and further visualized, thereby generating a heat map representation of the occlusal contacts of the subject's teeth. Further, the heat map representation of the occlusal contacts of the subject' teeth may be used, for example, by a practicing clinician, for the modelling positions of the subject's teeth.

However, determining the occlusal contacts on the 3D mesh models may require a greater amount of computational resources of a processor. Certain approaches addressing the above-identified technical problem have been proposed in the prior art.

PCT Application Publication No.: 2020/181973-A1 published on Sep. 17, 2020, assigned to Hangzhou Zoho Information Technology Co. Ltd., and entitled "Method for Determining Occlusion Relationship between Maxillary Teeth and Mandibular Teeth, and Computer System" discloses a computer-executed method for determining an occlusion relationship between maxillary teeth and mandibular teeth, said method comprising: acquiring a three-dimensional digital model of the maxillary teeth and mandibular teeth; and determining, on the basis of the three-dimensional digital model of the maxillary teeth and mandibular teeth, an occlusion relationship between the maxillary teeth and mandibular teeth by means of a point cloud registration method.

U.S. Pat. No. 6,334,853-B1 issued on Jan. 1, 2002, assigned to Align Technology Inc., and entitled "Method for Obtaining a Dental Occlusion Map" discloses a method for obtaining a dental occlusion map of a three-dimensional virtual computer model of teeth of upper and lower jaws of a mouth. The occlusion map indicates the distances between opposite regions on facing surfaces of opposite teeth of the upper and lower jaws of the mouth. The method includes the steps of determining the distances between opposite regions on opposite teeth of the upper and lower jaws of the mouth, and setting up a correspondence between the determined distances and regions on a mapping surface.

U.S. Pat. No. 10,695,146-B1 issued on Jun. 30, 2020, assigned to Oxilio Ltd., and entitled "Systems and Methods for Determining Orthodontic Treatments" discloses methods of determining an orthodontic treatment comprising: obtaining 3D model of simulated position of teeth following proposed orthodontic treatment; the 3D model comprising a point cloud representation having vector points representative of teeth surface; generating an axis aligned boundary box around each tooth; identifying a pair of tooth-tooth bounding boxes of adjacent teeth that intersect; defining an area of overlap of the pair of tooth-tooth bounding boxes; mapping the area of overlap onto the plurality of vector points, the plurality of vector points populating a 3D grid, having cells, of a simulation space; identifying a subset of the cells including the mapped overlap area, and for only the subset of the cells determining a distance between the vector points relating to adjacent teeth; and determining the proposed orthodontic treatment as the determined orthodontic treatment if the determined distance is more than a predetermined distance.

SUMMARY

It is an object of the present technology to ameliorate at least some of the inconveniences present in the prior art.

Developers of the present technology have appreciated that it may be advantageous, in terms of saving the computational resources, to determine the occlusal contacts of the lower teeth relative to the upper teeth of the subject based on respective point cloud 3D representations thereof.

Broadly speaking, a point cloud 3D representation of an object refers to a representation thereof where a surface of the object is represented by points, each of which is defined by a vector, such as a vector of coordinates (x, y, z) in an associated coordinate system.

Also, the developers have realized that to determine the distances between the respective occlusal surfaces of the lower teeth and the upper teeth of the subject at a certain level of accuracy, not all the points of the point cloud 3D representations of the subject's teeth need to be considered. More specifically, the non-limiting embodiments of the present methods and systems are directed to determining points of the point cloud 3D representations that are more indicative of occlusal contacts between the subject's teeth and omitting from further consideration those that are less indicative thereof. For example, in at least some non-limiting embodiments of the present technology, such points of the point cloud 3D representations may be associated with minimum distances between the respective occlusal surfaces.

By doing so, the present methods and systems may allow filtering out points of the point cloud 3D representations of the subject's teeth that may be less representative of the occlusal contacts therebetween. By considering fewer than the total number of points, a reduction of computational power of the processor may be required, which may further allow for a more efficient modelling of the tooth movements of the subject's teeth.

More specifically, in accordance with a first broad aspect of the present technology, there is provided a method of determining occlusal contacts between lower teeth and upper teeth of a subject. The method is executable by a processor of an electronic device. The method comprises: receiving, by the processor, a 3D model including a first portion and a second portion: the first portion including a first plurality of points representative of a surface of a lower arch form of the subject including the lower teeth; and the second portion including a second plurality of points representative of a surface of an upper arch from of the subject including the upper teeth; determining an occlusal plane associated with the second portion of the 3D model; determining, from each one of the first plurality of points, respective distance values to the occlusal plane; identifying, in the first plurality of points, based on the respective distance values, a set of occlusal points representative of at least some of the occlusal contacts between the lower teeth and the upper teeth, the identifying comprising: generating a voxel grid for the second portion of the 3D model, each voxel of the voxel grid including a respective set of points from the first plurality of points; determining, in a given set of points, a single point representative of an occlusal contact between the lower teeth and the upper teeth within a respective one of the voxel grid; mapping, on at least one of the second portion of the 3D model and the first portion of the 3D model, at each one of the set of occlusal points, respective distance values associated therewith, thereby generating a depth map representation of the at least some of the occlusal contacts between the lower teeth and the upper teeth; storing data indicative of the depth map representation in a memory device communicatively coupled with the processor.

In some implementations of the method, the determining the single point comprises determining a point with a minimum respective distance value in the respective one of the voxel grid of the first portion of the 3D model.

In some implementations of the method, the determining the single point further comprises applying a Bounding Volume Hierarchy algorithm to the respective one of the voxel grid.

In some implementations of the method, the determining, from each one of the first plurality of points, the respective distance values comprises determining a distance field associated with the second portion of the 3D model.

In some implementations of the method, the determining the respective distance values further comprises: determining, from each one of the first plurality of points, along a respective normal vector to the occlusal plane, respective orthogonal distance values; determining, from each one of the first plurality of points, along a predetermined rotational trajectory of the first portion relative to the second portion of the 3D model to the occlusal plane, respective arc distance values.

In some implementations of the method, the method further comprises determining the predetermined rotational trajectory of the first portion of the 3D model relative to the second portion of the 3D model based on data of at least one mandibular condyle of the subject.

In some implementations of the method, the determining the predetermined rotational trajectory comprises determining, based on the data of the at least one mandibular condyle, a rotation center of the first portion relative to the first portion of the 3D model.

In some implementations of the method, the determining the predetermined rotational trajectory further comprises determining a bite position between the first portion and the second portion of the 3D model.

In some implementations of the method, the identifying the set of occlusal points further comprises: determining, based on the respective orthogonal distance values, an orthogonal subset of occlusal points; determining, based on the respective arc distance values, an arc subset of occlusal points; and merging the orthogonal subset of occlusal points and the arc subset of occlusal points.

In some implementations of the method, the lower arch form further includes a lower gingiva, and the method further comprises, prior to the determining the respective distance values: identifying, within the first plurality of points, point representative of the lower gingiva; and removing, from the first portion of the 3D model, the points representative of the lower gingiva from further consideration.

In some implementations of the method, the method further comprises causing, by the processor, display of the depth map representation on the at least one of the first portion and the first portion of the 3D model.

In some implementations of the method, the depth map representation is for determining an orthodontic treatment for the subject.

In accordance with a second broad aspect of the present technology, there is provided a system for determining occlusal contacts between lower teeth and upper teeth of a subject. The system comprises an electronic device including: a processor and a non-transitory memory device storing instructions. The processor, upon executing the instructions, is configured to: receive a 3D model including a first portion and a first portion: the first portion including a first plurality of points representative of a surface of a lower arch form of the subject including the lower teeth; and the second portion including a first plurality of points representative of a surface of an upper arch from of the subject including the upper teeth; determine an occlusal plane associated with the second portion of the 3D model; determine, from each one of the first plurality of points, respective distance values to the occlusal plane; identify, in the first plurality of points, based on the respective distance values, a set of occlusal points representative of at least some of the occlusal contacts between the lower teeth and the upper teeth, the identifying comprising: generating a voxel grid for the first portion of the 3D model, each voxel of the voxel grid including a respective set of points from the first plurality of points; determining, in a given set of points, a single point representative of an occlusal contact between the lower teeth and the upper teeth within a respective one of the voxel grid; map, on at least one of the first portion of the 3D model and the first portion of the 3D model, at each one of the set of occlusal points, respective distance values associated therewith, thereby generating a depth map representation of the at least some of the occlusal contacts between the lower teeth and the upper teeth; store data indicative of the depth map representation in the non-transitory memory device.

In some implementations of the system, the processor is configured to determine the single point as being a point with a minimum respective distance value in the respective one of the voxel grid of the first portion of the 3D model.

In some implementations of the system, to determine the single point, the processor is configured to apply a Bounding Volume Hierarchy algorithm to the respective one of the voxel grid.

In some implementations of the system, to determine the respective distance values, the processor is configured to determine a distance field associated with the second portion of the 3D model.

In some implementations of the system, to determine the respective distance values, the processor is further configured to: determine, from each one of the first plurality of points, along a respective normal vector to the occlusal plane, respective orthogonal distance values; determine, from each one of the first plurality of points, along a predetermined rotational trajectory of the first portion relative to the second portion of the 3D model to the occlusal plane, respective arc distance values.

In some implementations of the system, to identify the set of occlusal points, the processor is further configured: determine, based on the respective orthogonal distance values, an orthogonal subset of occlusal points; determine, based on the respective arc distance values, an arc subset of occlusal points; and merge the orthogonal subset of occlusal points and the arc subset of occlusal points.

In some implementations of the system, the lower arch form further includes a lower gingiva, and the processor is further configured to, prior to determining the respective distance values: identify, within the first plurality of points, point representative of the lower gingiva; and remove, from the first portion of the 3D model, the points representative of the lower gingiva from further consideration.

In some implementations of the system, the processor is further configured to cause display of the depth map representation on the at least one of the first portion and the first portion of the 3D model.

In the context of the present specification, the term "orthodontic treatment" is broadly referred to as any type of medical intervention aimed at correcting malocclusions associated with the subject's teeth, including surgical and non-surgical manipulations, such as, but not limited to, using aligners. Further, the orthodontic treatment, as referred to herein, may be determined by a professional practitioner in the field of dentistry (such as an orthodontist, a maxillofacial surgeon, for example), automatically by a specific software, based on respective image data and input parameters associated with the subject, and/or a combination of manual and automatic.

Further, in the context of the present specification, the term "point cloud 3D representation" of an object (such as a subject's arch form) refers to an image thereof, for example, in a three-dimensional space, comprising a plurality of data points, each of which is defined by a respective set of coordinates (x, y, z), thereby representing a surface of the object. In one example, the point cloud 3D representation of the object may be generated by an imaging device such as a 3D laser scanner, where each laser scan corresponds to a respective data point. Further, the laser scans can be merged, or otherwise registered relative to each other, generating the point cloud 3D representation.

In another example, the point cloud 3D representation of the object may be generated by converting a series of 2D images (or a panoramic video) thereof taken from different angles using, for example, specific software.

In yet another example, the point cloud 3D representation may be generated from a respective mesh 3D representation of the object by omitting data of edges defining mesh elements within the respective 3D mesh model and preserving only data of vertices thereof.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

Certain aspects and embodiments of the present technology are directed to methods of and systems for manufacturing an orthodontic appliance based on orthodontic methods determined using occlusal contacts determined as described and claimed herein.

More specifically, certain aspects and embodiments of the present technology comprise a computer-implemented method of determining occlusal contacts between upper teeth and lower teeth of the subject based on point cloud 3D representations thereof, and further, based on the so determine occlusal contacts, modelling tooth movements of the subject's teeth to determine the orthodontic treatment for the subject. Additionally, the determining the occlusal contacts may be conducted after the determining the orthodontic treatment, for example, for verification thereof in terms of its safety and/or efficacy. For example, the verification of the determined orthodontic treatment may include modelling effect of the orthodontic appliance onto the subject's teeth.

Certain embodiments of the present technology minimize, reduce or avoid some of the problems noted with the prior art. For example, by implementing certain embodiments of the present technology in respect of determining the occlusal contacts between the subject's teeth, one or more of the following advantages may be obtained: processing fewer points of the point cloud 3D representations for determining the occlusal contacts, which may allow reducing computational resources consumption on modelling the tooth movements of the subject's teeth. Thus, methods and systems provided herein, according to certain non-limiting embodiments of the present technology, allow determining the occlusal contacts between the subject's teeth using fewer points of the point cloud 3D representations without compromising accuracy thereof, whilst reducing a required computational resource of the processor for devising the orthodontic treatment for the subject.

Orthodontic Treatment

Figure 1:
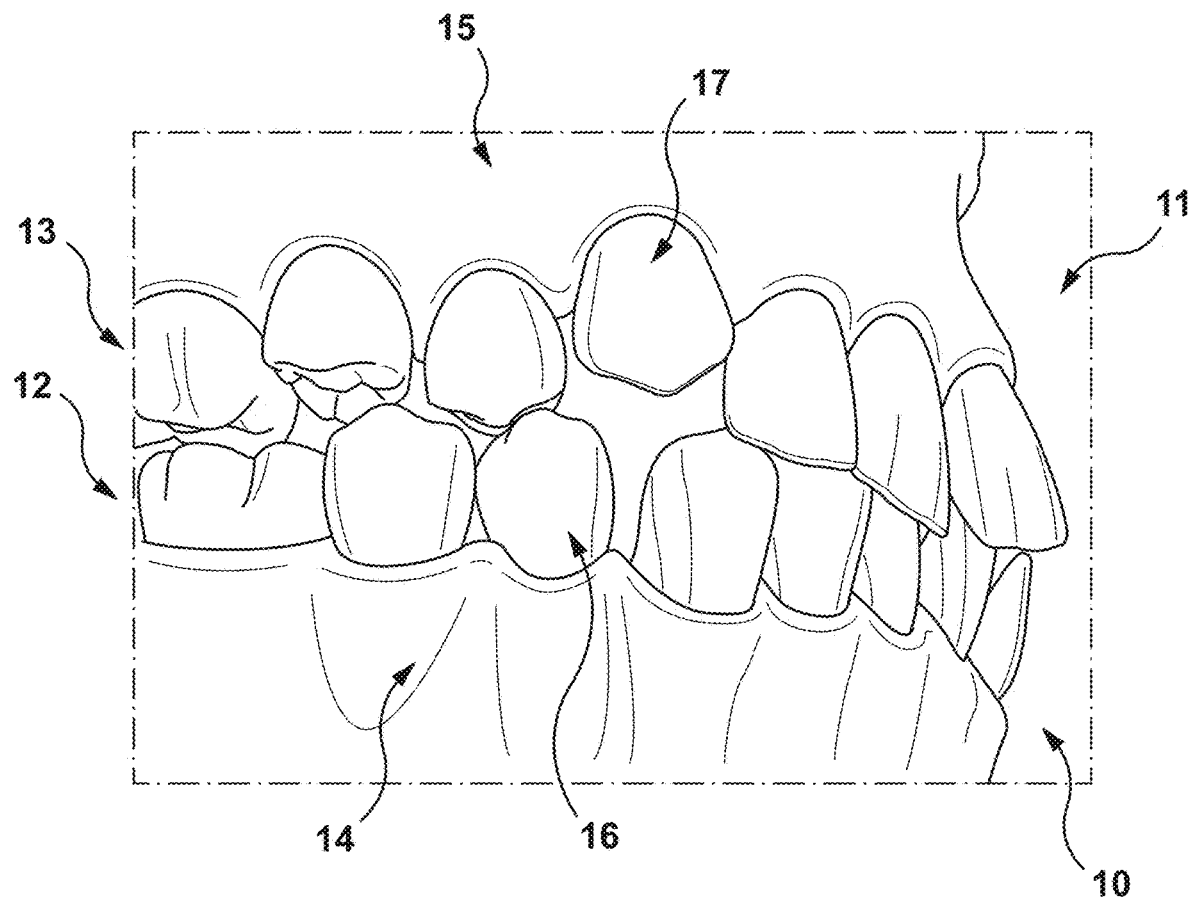
FIG. 1 depicts a perspective view of a lower arch form of a subject depicting examples of malocclusions of some of subject's teeth, in accordance with certain non-limiting embodiments of the present technology.

With initial reference to FIG. 1, there is depicted a perspective view of a lower arch form 10 and an upper arch form 11 of the subject (not depicted), to which certain aspects and non-limiting embodiments of the present technology may be applied.

As can be appreciated, the lower arch form 10 includes lower teeth 12 and a lower gingiva 14; and the upper arch from 11 includes upper teeth 13 and upper gingiva 15. Further, in the depicted embodiments of FIG. 1, positions of at least some of the lower teeth 12 within the lower arch form 10 and those of the upper teeth 13 within the upper arch form 11 may be indicative of certain orthodontic disorders of the subject. For example, at least a given lower tooth 16 and a given upper tooth 17 are misaligned within a respective one of the lower arch from 10 and the upper arch from 11. Further, as the given lower tooth 16 is abnormally embedded within the lower teeth 12 while the given upper tooth 13 is abnormally protrudes over opposing ones of the lower teeth 12, the misalignment thereof may affect a state of normal occlusion of the lower teeth 12 relative to the upper teeth 13 or, in other words, cause a malocclusion therebetween—that is, an irregular spatial relationship between the lower teeth 12 and the upper teeth 13.

Other malocclusions (not depicted) associated with misalignment of lower teeth 12 relative to each other and the upper teeth 13, according to certain non-limiting embodiments of the present technology, may include, without limitation: overbites, underbites, crossbites, openbites, crowding of some of the lower teeth 12 and the upper teeth 13, midline shift therebetween, and others.

In some non-limiting embodiments of the present technology, for resolving the above-mentioned malocclusions, an orthodontic treatment may be provided to the subject.

In some non-limiting embodiments of the present technology, the orthodontic treatment may comprise applying an orthodontic appliance. Generally speaking, the orthodontic appliance may be configured to exert a respective predetermined force onto at least some of the lower teeth 12 and the upper teeth 13—such as the given lower tooth 16 and the given upper tooth 17, causing them to move towards an aligned position, thereby restoring the state normal occlusion of the lower teeth 12 relative to upper teeth 13 of the subject. More specifically, in the depicted embodiments of FIG. 1, the orthodontic appliance may be configured to cause the given lower tooth 16 to move outwardly between lower teeth adjacent thereto; and further cause clockwise rotation thereof. Further, the orthodontic appliance may be configured to cause the given upper tooth 17 to move inwardly. In various non-limiting embodiments of the present technology, the orthodontic appliance may comprise orthodontic appliances of different types, shapes, sizes and configurations, such as those including, without limitation, aligners, brackets, multi-strand wires, strips, retainers, and plates.

In some non-limiting embodiments of the present technology, the orthodontic appliance may be selected, in the course of the orthodontic treatment to correct a respective malocclusion. For example, in some non-limiting embodiments of the present technology, the orthodontic appliance may include a biteplate (not depicted) used for correcting the overbites. More specifically, the biteplate may be configured for preventing front ones of upper teeth 13 overlap front ones of the lower teeth 12 for extended periods of time.

Further, in some non-limiting embodiments of the present technology, the orthodontic appliance may include a bitesplint (not depicted), which may be applied to the lower teeth 12 for correcting the crossbites—a lateral misalignment of one of the lower arch form 10 and the upper arch form 11 resulting, for example, in buccal surfaces of some of the upper teeth 13 overlapping lingual surfaces of opposing ones thereto of the lower teeth 12. To that end, the bitesplint may be configured for preventing the subject from biting completely, which may further allow correcting the crossbites.

Figure 2:
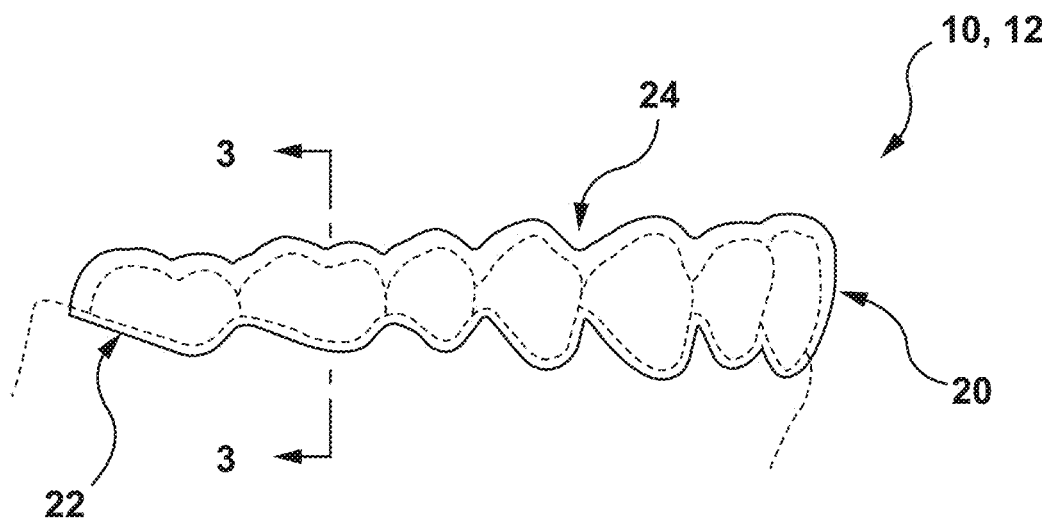
FIGS. 2 and 3 depict side and cross-sectional views, respectively, of a dental appliance applied to the subject's teeth that may be configured to treat the malocclusions of the subject's teeth present in FIG. 1, in accordance with certain non-limiting embodiments of the present technology.
Figure 3:
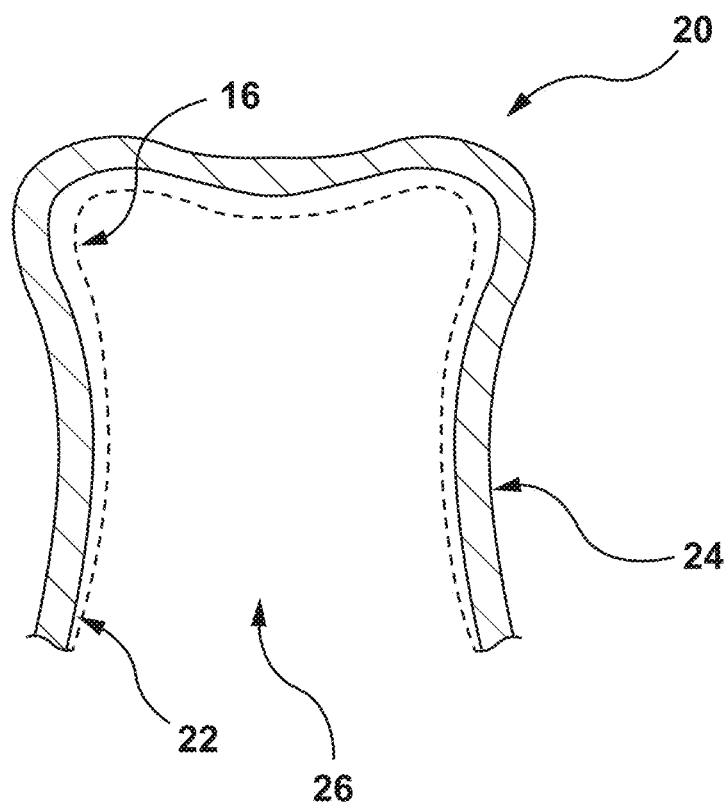

In specific non-limiting embodiments of the present the present technology, the orthodontic appliance may include application of at least one aligner. With reference to FIGS. 2 and 3, there is depicted an aligner 20 applied to at least some of the lower teeth 12, in accordance with certain non-limiting embodiments of the present technology. The aligner 20 comprises an inner surface 22 and an outer surface 24. The inner surface 22 defines a channel 26, which is configured, in some non-limiting embodiments of the present technology, for receiving crown portions of at least some of the lower teeth 12, such as the given lower tooth 16. However, in other non-limiting embodiments of the present technology, the channel 26 of the aligner 20 may be configured to receive crown portions of all of the lower teeth 12. At least one edge (also referred to herein as an "open edge") of the channel 26 is shaped for following a gum line (not depicted) along the lower gingiva 14.

It is appreciated that, in accordance with certain non-limiting embodiments of the present technology, the aligner 20 may be used for treating different teeth malocclusions, including but not limited to one or more of: closing interdental spaces ("space closure"), creating/widening interdental spaces, tooth rotation, tooth intrusion/extrusion, and tooth translation, to name a few. It should further be noted that in certain non-limiting embodiments of the present technology, applying the aligner 20 to the lower teeth 12 may further include applying specific attachments thereto.

As may become apparent, the aligner 20 may be designed in such a way that its inner surface 22 is configured to impose respective forces on one or more of the lower teeth 12 to obtain a desired position of the lower teeth 12 at a given stage of the orthodontic treatment.

Needles to say that, although in the depicted embodiments of FIGS. 2 and 3, the aligner 20 is configured to be applied onto the lower teeth 12, in other non-limiting embodiments of the present technology, a respective configuration of the aligner 20 may be applied to the upper teeth 13 of the subject for treating misalignment of at least some thereof—such as the given upper tooth 17. By so doing, the normal occlusion between the lower teeth 12 and the upper teeth 13 may be attained.

According to certain non-limiting embodiments of the present technology, the aligner 20 may be made of a polymer, such as a thermoplastic material. In other non-limiting embodiments of the present technology, the aligner 20 may be made of poly-vinyl chloride (PVC). In yet other non-limiting embodiments of the present technology, the aligner 20 may be made of polyethylene terephthalate glycol (PETG). Other suitable materials can also be used to form the aligner 20.

In some non-limiting embodiments of the present technology, the aligner 20 may be manufactured using additive manufacturing techniques, such as 3D printing techniques where the aligner 20 is formed by printing according to a pre-generated 3D representation thereof.

In other non-limiting embodiments of the present technology, the aligner 20 may be produced by a thermoforming process where (1) an unfinished aligner is produced, using a preform, on a respective aligner mold (not depicted) associated with a respective stage of the orthodontic treatment, which is configured to shape the inner surface 22 of the aligner 20; and (2) the unfinished aligner is cut along a predetermined cut line to remove excess material therefrom, thereby producing the aligner 20, the predetermined cut line defining the at least one edge of the channel 26 of the aligner 20.

In specific non-limiting embodiments of the present technology, the aligner 20 may be manufactured in accordance with one or more methods described in a co-owned U.S. patent application Ser. No. 17/143,074 filed on Jan. 6, 2021, entitled "SYSTEMS AND METHODS FOR FORMING A DENTAL APPLIANCE,", the content of which is incorporated herein by reference in its entirety.

However, the application of the aligner 20 or other applied orthodontic treatment may cause certain undesired effects. Referring back to FIG. 1, let it be assumed that the aligner 20 (not depicted in FIG. 1) is worn over at least one of the lower arch form 10 and the upper arch form 11, thereby causing a respective one of the given lower tooth 16 and the given upper tooth 17 to move to the aligned position thereof. However, such an alignment may create an undesirable occlusion between the given lower tooth 16 and the given upper tooth 17. As it may be appreciated, such an undesirable occlusion may result in damage of at least one of the given lower tooth 16 and the given upper tooth 17 including, for example, an erosion, cracks, or chippings, which may cause discomfort (such as pain) and/or esthetic defects to the subject.

In order to form the aligner 20 allowing achieving desired occlusal relationship between the subject's teeth during the orthodontic treatment, it may be required, at the stage of planning the orthodontic treatment, to model movements of the at least one of the lower teeth 12 and the upper teeth 13 to ensure the aligner 20 would not cause any damage therebetween in the course of the orthodontic treatment. Further, to monitor the progress of the orthodontic treatment—such as if the lower teeth 12 and the upper teeth 13 are approaching a state of normal occlusion, it may be practical to monitor the mutual spatial relationship therebetween. To that end, determining occlusal contacts between the lower teeth 12 and the upper teeth 13 using 3D representation of the subject's arch forms may be required.

More specifically, the determining occlusal contacts, as described herein, refers to a procedure of determining distances between occlusal surfaces of opposing teeth—such as the lower teeth 12 and the upper teeth 13, at a given stage of the orthodontic treatment.

However, in cases where the 3D representations comprise mesh elements representative of surfaces of the lower arch form 10 and the upper arch form 11, the determining the occlusal contacts while modelling the movements of the lower teeth 12 relative to the upper teeth 13 in concert may be a resource-intensive task for a processor (such as a processor 550 depicted in FIG. 5) as it may be necessary to process a significant amount of graphic data representative of mesh vertices and/or mesh edges of the mesh elements.

Thus, certain non-limiting embodiments of the present technology are directed to methods and systems for determining occlusal contacts between the lower teeth 12 and the upper teeth 13 using point cloud 3D representations thereof, which comprise pluralities of points respectively representative of the lower arch form 10 and the upper arch form 11. More specifically, the present methods and systems may include: (1) determining an occlusal plane associated with the upper teeth 13; (2) determining, for each point of a point cloud 3D representation of the lower arch form 12, a respective distance value to the occlusal plane associated with the upper arch form 13; (3) generating a voxel grid over a point cloud 3D representation of the lower arch form 10; and (4) determining, in each voxel of the voxel grid, a single point associated with a minimum respective distance value therein. By doing so, certain non-limiting embodiments of the present technology are directed to determining, in the point cloud 3D representation associated with the lower arch form 10, a set of occlusal points omitting from further processing a number of points that is less representative of the occlusal contacts between the lower teeth 12 and the upper teeth 13, which may allow reducing computational cost for the determining the occlusal contact between the subject's teeth without affecting the accuracy thereof. This may further allow for a more efficient modelling of movements of the lower teeth 12 relative to the upper teeth 13. Thus, the methods and systems described herein can provide for a more efficient planning of the orthodontic treatment considering the safety thereof. By efficient planning is meant a faster processing of data to model the tooth movements to develop the orthodontic treatment for the subject.

How the set of occlusal points can be determined, in accordance with certain non-limiting embodiments of the present technology, will be described in greater detail below with reference to FIGS. 7 to 9.

System

Figure 4:
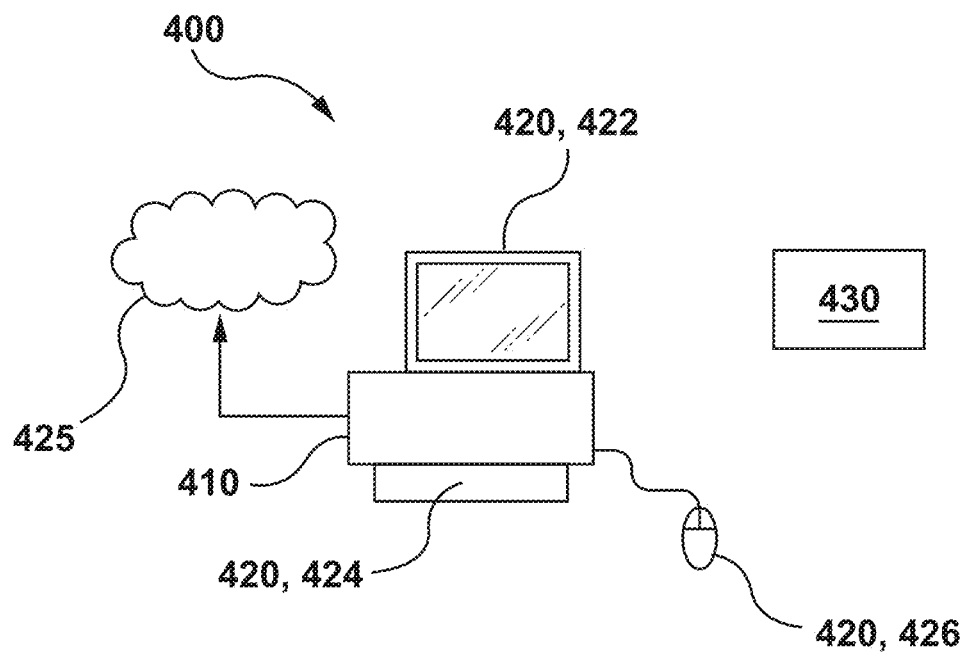
FIG. 4 depicts a schematic diagram of a system for determining occlusal contacts between the subject's teeth present in FIG. 1, in accordance with certain embodiments of the present technology.
Figure 5:
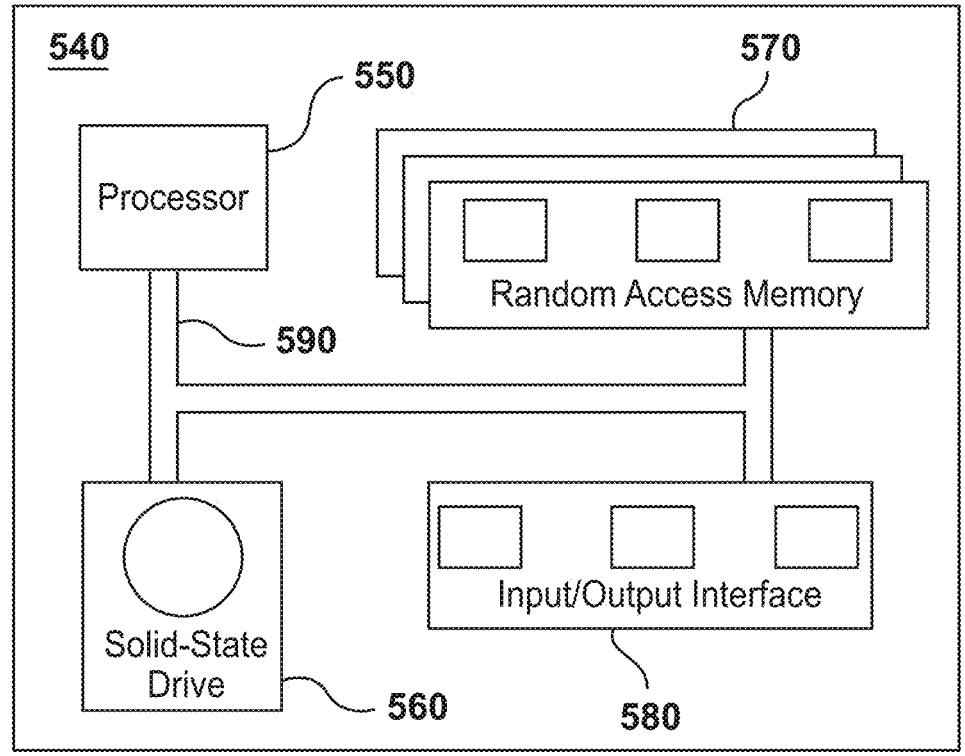
FIG. 5 depicts a schematic diagram of a computing environment of the system of FIG. 4, in accordance with certain embodiments of the present technology.

With reference to FIGS. 4 and 5, there is depicted a schematic diagram of a system 400 suitable for determining the occlusal contacts between the lower teeth 12 and the upper teeth 13, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to determine, based on image data associated with the subject, such as the point cloud 3D representations of the lower arch form 10 and the upper arch form 11, the occlusal contacts between the lower teeth 12 and the upper teeth 13. In additional non-limiting embodiments of the present technology, the computer system 410 may further be configured to model the movements of the at least one of the lower teeth 12 and the upper teeth 13 determining the occlusal contacts therebetween in real time for ensuring the aligner 20 produced based on the so planned orthodontic treatment would not cause any undesired effects, such as the collision between the given lower tooth 16 and the given upper tooth 17, as described above.

To that end, in some non-limiting embodiments of the present technology, the computer system 410 may be configured to receive the image data pertaining to the subject or to a given stage of the orthodontic treatment. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some non-limiting embodiments of the present technology, the image data includes datasets generally intended for the practice of periodontics.

In other non-limiting embodiments of the present technology, where the determining the occlusal contacts between the lower teeth 12 and the upper teeth 13 is used for verifying the effect of the aligner 20 thereon, the image data may further include a 3D representation of the aligner 20 prepared for manufacture thereof, for example, using 3D printing or thermoforming, as described above.

In some non-limiting embodiments of the present technology, the computer system 410 may be configured to receive the image data associated with the subject directly from an imaging device 430 communicatively coupled thereto. Broadly speaking, the processor 550 may be configured to cause the imaging device 430 to capture and/or process the image data of the lower teeth 12 and the periodontium (not depicted) of the subject. In certain non-limiting embodiments of the present technology, the image data may include, for example, one or more of: (1) images of external surfaces of respective crown portions of the lower teeth 12, (2) images of an external surface of the periodontium including those of the lower gingiva 14, the alveolar mandibular bone (not depicted), and images of superficial blood vessels and nerve pathways associated with the lower teeth 12; and (3) images of an oral region. By doing so, the imaging device 430 may be configured, for example, to capture image data of the lower arch form 10 of the subject. In another example, the imaging device may also be configured to capture and/or process image data of an upper arch form (not depicted) associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise an intra-oral scanner enabling to capture direct optical impressions of the at least one of the lower arch form 10 and the upper arch form 11 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 430 may comprise a desktop scanner enabling to digitize a mold (not depicted) representing the given configuration of the at least one of the lower arch form 10 and the upper arch form 11 associated with the respective stage of the orthodontic treatment. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from DENTAL WINGS, INC. of 2251, ave Letourneux, Montreal (QC), Canada, H1V 2N9. It should be expressly understood that the desktop scanner can be implemented in any other suitable equipment.

In yet other non-limiting embodiments of the present technology, the imaging device 430 can comprise a 3D laser scanner enabling to obtain a respective point cloud 3D representation of the at least one of the lower arch form 10 and the upper arch form 11—such as by scanning the mold thereof and thus registering three-dimensional coordinates of points representative of the surface of the mold.

In a specific non-limiting example, the 3D laser scanner can be of one of the types available from LASER DESIGN of 5900 Golden Hills Drive, Minneapolis, MN 55416. It should be expressly understood that the desktop scanner can be implemented in any other suitable equipment.

Further, it is contemplated that the computer system 410 may be configured for processing of the received image data. The resulting image data of the lower arch form 10 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

Further, with reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random-access memory 570 and an input/output interface 580. Communication between the various components of the computing environment 540 may be enabled by one or more internal and/or external buses 590 (e.g. a PCI bus, universal serial bus, IEEE 1394 "Firewire" bus, SCSI bus, Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 580 may implement specific physical layer and data link layer standard such as Ethernet™, Fibre Channel, Wi-Fi™ or Token Ring™. The specific physical layer and the data link layer may provide a base for a full network protocol stack, allowing communication among small groups of computers on the same local area network (LAN) and large-scale network communications through routable protocols, such as IP.

According to implementations of the present technology, the solid-state drive 560 stores program instructions suitable for being loaded into the random-access memory 570 and executed by the processor 550, according to certain aspects and embodiments of the present technology. For example, the program instructions may be part of a library or an application.

In some non-limiting embodiments of the present technology, the computing environment 540 is implemented in a generic computer system, which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Image Data

As alluded to above, according to certain non-limiting embodiments of the present technology, the processor 550 may be configured to: (1) receive image data indicative of current configurations of each one of the lower arch form 10 and the upper arch form 11; (2) determine, based on the image data, the occlusal contacts between the lower teeth 12 and the upper teeth 13; and (3) determine and/or verify, based on the occlusal contacts, the orthodontic treatment for the subject. Optionally, in some non-limiting embodiments of the present technology, the processor 550 may further be configured to cause the manufacture of the aligner 20 based on the so determined orthodontic treatment, as described above.

Figure 6:
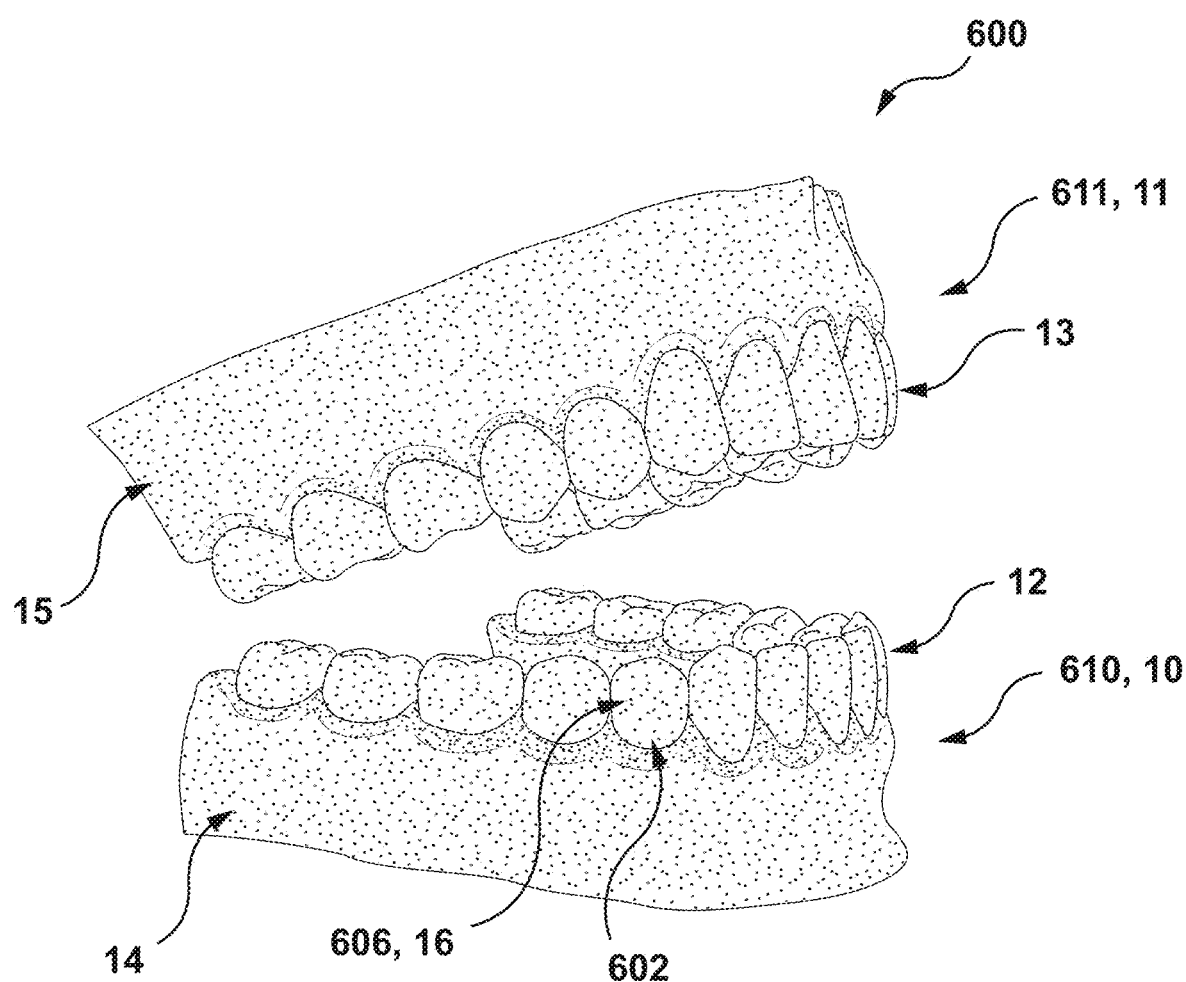
FIG. 6 depicts a 3D model including a point cloud representative of the subject's teeth present in FIG. 1 used, by a processor of FIG. 5, to determine the occlusal contacts therebetween, in accordance with certain non-limiting embodiments of the present technology.

With reference to FIG. 6, there is depicted a perspective view of a 3D model 600 including a first portion 610 and a second portion 611 respectively representative of current configurations of the lower arch form 10 and the upper arch form 11, in accordance with certain non-limiting embodiments of the present technology.

As noted hereinabove, in some non-limiting embodiments of the present technology, the 3D model 600 may be a point cloud 3D representation of the arch forms of the subject where the first portion 610 and the second portion 611 include plurality of points respectively representative of surfaces of the lower arch form 10 and the upper arch form 11.

In some non-limiting embodiments of the present technology where the imaging device 430 is the 3D laser scanner, the processor 550 may be configured to receive the 3D model 600 as taken by the imaging device 430. In other non-limiting embodiments of the present technology, where the imaging device 430 is a conventional intraoral scanner providing 3D representations of objects including 3D meshes (such as triangular meshes and the like), the processor 550 may be configured to pre-process the 3D model 600 to remove image data representative of the mesh edges therefrom leaving only image data representative of the mesh vertices.

It should be noted that it is not limited how points are distributed within the 3D model 600 is not limited; and in some non-limiting embodiments of the present technology, the points may be distributed uniformly within the 3D model 600. However, in other non-limiting embodiments of the present technology, the points may have variable distribution within the 3D model 600, such as have higher density in regions representative of lower teeth 12 and the upper teeth 13 and have lower density in the regions representative of lower gingiva 14 and upper gingiva 15.

In some non-limiting embodiments of the present technology, the processor 550 may be configured to determine a bite position between the first portion 610 and the second portion 611 corresponding to a position between the lower teeth 12 and the upper teeth 13 while the subject's mouth is closed. In some non-limiting embodiments of the present technology, the processor 550 may be configured to determine the bite position by determining a correspondence between specific reference points (not depicted) on each one of the first portion 610 and the second portion 611.

However, in other non-limiting embodiments of the present technology, the processor 550 may be configured to determine the bite position between the first portion 610 and the second portion 611 using a remoteness measure optimization approach as described in co-owned U.S. patent application Ser. No. 17/319,666 filed on May 13, 2021, entitled "SYSTEMS AND METHODS FOR DETERMINING A BITE POSITION BETWEEN TEETH OF A SUBJECT," which is concurrently filed with the present patent application, and the content of which is incorporated herein by reference in its entirety. More specifically, in these embodiments, the processor 550 may be configured to: (i) receive the 3D model 600 including the first portion 610 and the second portion 611; (ii) identify, for each point of the first portion 610 of the 3D model 600, a respective initial position relative to the second portion 611 of the 3D model 600; (iii) determine, for each point of the first portion 610 of the 3D model 611, based on the respective initial position, a respective distance value therefrom to the second portion 611 of the 3D model 600; (iv) determine, for each point of the first portion 610 of the 3D model 600, a respective weight value, the respective weight value associated with a given point of the first portion 610 of the 3D model 600 being indicative of a curvature of the first portion 610 of the 3D model 600 thereat; (v) generate, for each point of the first portion 610 of the 3D model 600, based on the respective weight value and the respective distance value associated therewith, a respective weighted distance value; (vi) aggregate respective weighted distance values associated with each point of the first portion 610 thereby determining an aggregate distance value, the aggregate distance value being indicative of a remoteness measure of a current position of the first portion 610 of the 3D model 600 from a bite position thereof relative to the second portion 611 of the 3D model 600; (vii) and determine the bite position between the lower teeth 12 and the upper teeth 13 based on the aggregate distance value associated with the first portion 610 of the 3D model 600.

Further, in some non-limiting embodiments of the present technology, the processor 550 may be configured to segment, in the 3D model 600, respective tooth 3D representations of each one of the lower teeth 12 and the upper teeth 13—such as a respective tooth 3D representation 606 of the given lower tooth 16 in the first portion 610 of the 3D model. To that end, in some non-limiting embodiments of the present technology, the processor 550 may be configured to determine a tooth-gingiva segmentation loop 602 segmenting the respective tooth 3D representation 606 from a lower gingiva 3D representation (not separately labelled) of the lower gingiva 14.

In some non-limiting embodiments of the present technology, the processor 550 may be configured to obtain the tooth-gingiva segmentation loop 602 having been previously generated by third-party software, based on the 3D model 600, and data indicative thereof may have been stored in a data format, in which the processor 550 may be configured to receive it, for example, via the input/output interface 580.

In other non-limiting embodiments of the present technology, the tooth-gingiva segmentation loop 602 may be generated manually, for example, by the practicing clinician involved in the determining the orthodontic treatment. For example, the practicing clinician may manually apply the tooth-gingiva segmentation loop 602 onto the 3D model 600, using respective suitable software, and the processor 550 may further be configured to receive the 3D model 600, and detect the tooth-gingiva segmentation loop 602 applied thereon.

In specific non-limiting embodiments of the present technology, the processor 550 may be configured to determine the tooth-gingiva segmentation loop 602 based on analyzing spatial curvature of the respective tooth 3D representation 602 and that of the lower gingiva 3D representation (not separately labelled). More specifically, in this regard, the processor 550 may be configured to apply one of the approaches described in a co-owned U.S. Pat. No. 10,695, 147-B1 issued on Jun. 30, 2020, entitled "METHOD AND SYSTEM FOR DENTAL BOUNDARY DETERMINATION"; the content of which is hereby incorporated by reference in its entirety.

More specifically, according to certain non-limiting embodiments of the present technology, in order to determine the tooth-gingiva segmentation loop 602, the processor may be configured to: (i) receive the 3D model 600 of the upper arch form 20; (ii) define, around the respective tooth 3D representation, a given tooth-gingiva segmentation loop prototype around it of the tooth-gingiva segmentation loop 602; (iii) for each point of a plurality of points of the given tooth-gingiva segmentation loop prototype, determine an indication of curvature thereof; (iv) determine, based on the indication of curvature corresponding to the respective point, a predicted likelihood parameter for each point of the plurality of points, wherein the predicted likelihood parameter may indicate a predicted likelihood that a respective point corresponds to the tooth-gingiva segmentation loop 602 between the given lower tooth 16 and the lower gingiva 14; and (v) use the predicted likelihood parameter of the respective vertices to select the vertices defining the tooth-gingiva segmentation loop 602.

Further, in some non-limiting embodiments of the present technology, the processor 550 may be configured to remove the so identified lower gingiva 3D representation of the lower gingiva 14, from the first portion 610 of the 3D model 600, thereby omitting points thereof from further processing for determining the occlusal contacts between the lower teeth 12 and the upper teeth 13.

It should be noted that in some non-limiting embodiments of the present technology the processor 550 may also be configured to apply the approach described above to identifying and removing points of representative of the lower gingiva 14, mutatis mutandis, to the second portion 611 of the 3D model 600.

Thus, using the 3D model 600 and based on data indicative of the bite position between the first portion 610 and the second portion 611 thereof, in accordance with certain non-limiting embodiments of the, the processor 550 may be configured to determine respective distance values between points of the first portion 610 and the second portion 611, and further, based on the so determined respective distance values, determine the occlusal contacts between the lower teeth 12 and the upper teeth 13.

Determining Distances Between Opposing Teeth

Figure 7:
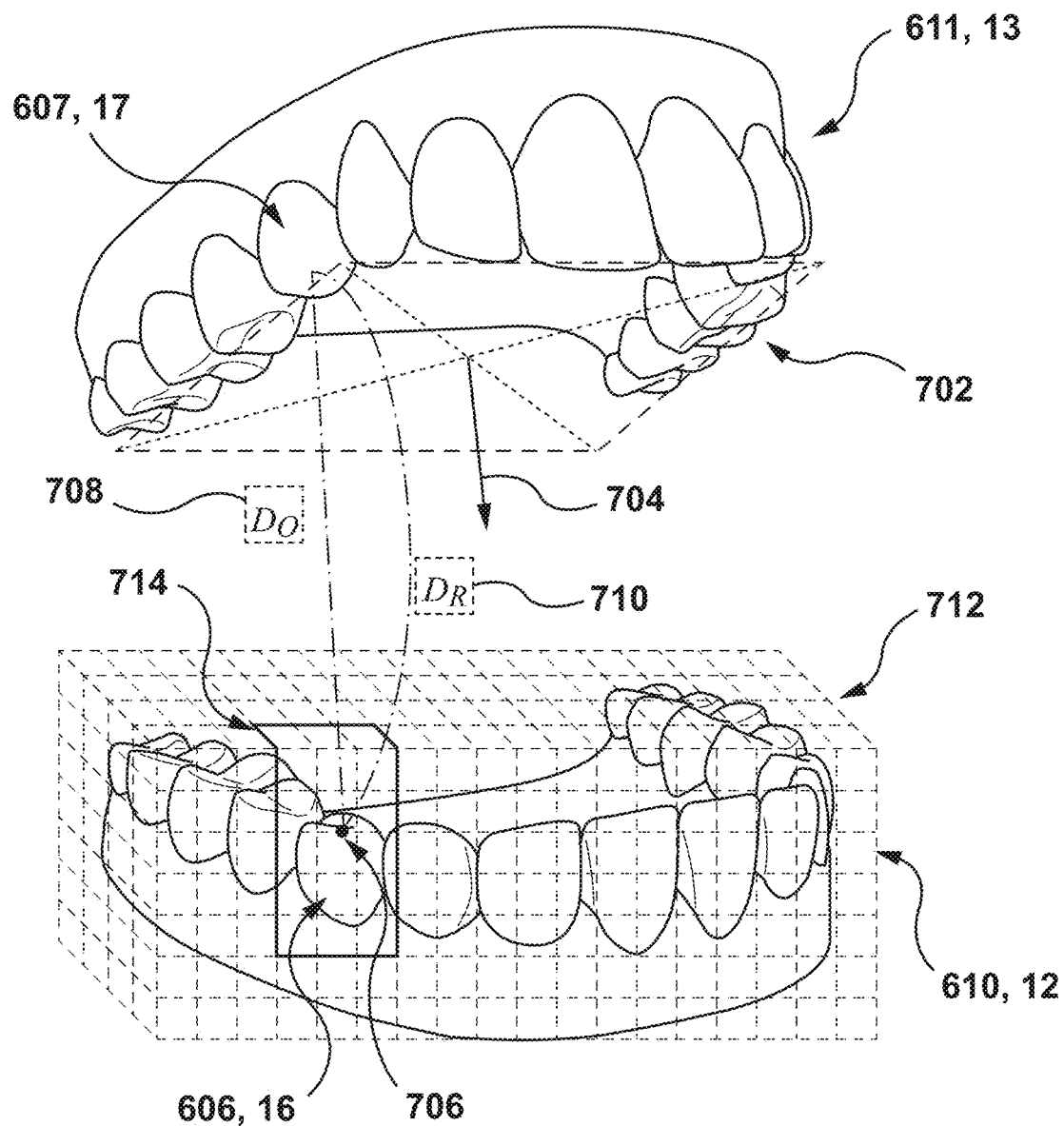
FIG. 7 depicts a schematic diagram of a step for determining, by a processor of FIG. 5, using the 3D model of FIG. 6, respective distance values between points representative of opposing ones of the subject's teeth present in FIG. 1, in accordance with certain non-limiting embodiments of the present technology.

With reference to FIG. 7, there is depicted a schematic diagram of a step for determining, by the processor 550, the respective distance values between the points of the first portion 610 and the second portion 611 of the 3D model 600, in accordance with certain non-limiting embodiments of the present technology.

In some non-limiting embodiments of the present technology, to determine the respective distance values between each point of the first portion 610 and the second portion 611, the processor 550 may be configured to determine a signed distance field (not depicted) associated with the second portion 611. More specifically, the processor 550 may be configured to (1) convert the second portion 611 into a voxel space; (2) assign, to each voxel positioned inside the second portion 611, a respective negative distance value from a surface of the second portion 611; and (3) assign, to each voxel position outside the second portion 611, a respective positive distance value from the surface of the second portion 611. Thus, the processor 550 may be configured to determine, based on the so defined signed distance field (not depicted), a respective distance value associated with a given point 706 of the first portion 610 as a shortest path therefrom to the second portion 611.

As it may become apparent, in these embodiments, a level of accuracy of the determining the respective distances between each point of the first portion 610 and the second portion 611 of the 3D model 600 may depend on a level of granularity of the voxel space associated with the second portion 611.

However, in other non-limiting embodiments of the present technology, the processor 550 may be configured to determine the respective distance values between the first portion 610 and the second portion 611 as distances between each point of the first portion 610 and an upper occlusal plane 702 associated with the upper teeth 13.

In some non-limiting embodiments of the present technology, the processor 550 may be configured to determine the upper occlusal plane 702 as a plane extending through incisal edges of incisors (not separately labelled) and cusps of occluding surfaces of posterior ones (not separately labelled) of the upper teeth 13. In other non-limiting embodiments of the present technology, the upper occlusal plane 702 associated with the upper teeth 13 may be predetermined by the practicing clinician, using, a specific articulator, as an example. It should be expressly understood that other techniques to determining the upper occlusal plane 702 associated with the upper teeth 13 may also be used without departing from the scope of the present technology.

Further, for a more accurate modelling of the movements of the lower teeth 12 relative to the upper teeth 13, in some non-limiting embodiments of the present technology, the processor 550 may be configured to determine, for each point of the first portion 610 of the 3D model 600, the respective distance values including: (1) respective orthogonal distance values to the upper occlusal plane 702, which can be used for determining the occlusal contacts when modelling translational movements of the lower teeth 12 relative to the upper teeth 13; and (2) respective arc distance values to the upper occlusal plane 702, which can be used for determining the occlusal contacts when modelling rotational movements of the lower teeth 12 relative to the upper teeth 13. With continued reference to FIG. 7, these two parameters used for the determining the occlusal contacts between the lower teeth 12 and the upper teeth 13, in accordance with certain non-limiting embodiments of the present technology, will be described in greater detail.

According to certain non-limiting embodiments of the present technology, the processor 550 may be configured to determine the respective orthogonal distances along an occlusal plane normal vector 704 of the upper occlusal plane 702. For example, the processor 550 may be configured to determine a respective orthogonal distance value 708 Do from the given point 706 of the first portion 610 to the upper occlusal plane 702 associated with the upper teeth 13. In other words, the processor 550 may be configured to determine the respective orthogonal distance 708 as a distance covered by the given point 706 of the first portion 610 while the first portion 610 performs a translational movement relative to the second portion 611—that is, moves along a respective perpendicular dropped from the given point 706 to the upper occlusal plane 702.

Further, according to certain non-limiting embodiments of the present technology, to determine the respective arc distance values between the points of the first portion 610 to the upper occlusal plane 702, first, the processor 550 may be configured to determine a rotational trajectory of the lower teeth 12 relative to the upper teeth 13. To that end, in some non-limiting embodiments of the present technology, first, the processor 550 may be configured to receive data of mandibular condyles (not depicted) of the lower arch form 10—for example, as part of data of a subject's skull—and further, based on this data, determine a rotation axis of the lower arch from 10 as an axis extending through the mandibular condyles.

For example, in some non-limiting embodiments of the present technology, the processor 550 may be configured to register multiple predetermined positions of a given point (such as the given point 706) associated with the lower arch form 10 relative to the subject's cranium (for example, the upper arch from 11) in respective 3D scans (such as a computed tomography scans or magnetic resonance imaging scans, as an example) of the subject's skull as the subject opens and/or closes their mouth. Further, based on the so registered multiple predetermined positions of the given point 706 relative to the upper arch form 11, the processor 550 may be configured to determine locations of respective rotation centers of mandibular condyles of the lower arch form 10 in temporomandibular joints (TMJs) of the subject's skull; and thus, construct the rotation axis extending through the respective rotation centers.

However, in other non-limiting embodiments of the present technology, the processor 550 may be configured to determine the rotation axis associated with the lower arch form 10 based on 2D scans of the subject's skull—such as a lateral radiograph thereof, as an example. For example, the processor 550 may be configured to conduct a cephalometric analysis of the subject's skull, based on the 2D scans thereof, to determine the locations of the respective rotation centers of the lower arch form 10 as points of intersection of lines extending through certain anatomical reference points associated with the subject's skull. In specific non-limiting embodiments of the present technology, the processor 550 may be configured to conduct the cephalometric analysis to determine the respective rotation centers as described in a co-owned U.S. Pat. No. 10,898,298-B1, issued on Jan. 26, 2021 and entitled "SYSTEMS AND METHODS FOR DETERMINING AN ORTHODONTIC TREATMENT", the content of which is incorporated herein by reference in its entirety.

More specifically, the processor 550 can be configured to: (i) receive the image data including data relating to the lower arch form 10 and the cranium portion of the skull; (ii) identify, from the image data, a first pair of reference points for defining a first reference line, the first pair of reference points including an Articulare point and a Gnathion point of the skull of the subject; (iii) identify, from the image data, a second pair of reference points for defining a second reference line, the second pair of reference points including a Basion point and an Orbitale point of the skull; the second reference line intersecting with the first reference line; (iv) generate, based on the first pair of reference points, the first reference line; (v) generate, based on the second pair of reference points, the second reference line; and (vi) determine, based on an intersection of the first reference line and the second reference line, one of the respective rotation centers for the lower arch form 10.

Thus, based on the so determined rotation axis associated with the lower arch form 10, the processor 550 may be configured to determine the rotational trajectory of the lower arch form 10 relative to the upper arch form 11 and further determine the respective arc distance values of each point of the first portion 610 to the upper occlusal plane 702 along the rotational trajectory. For example, the processor 550 may be configured to determine a respective arc distance value 710 DR from the given point 706 of the first portion 610 to the upper occlusal plane 702 along the rotational trajectory.

Further, instead of determining a given one of the respective orthogonal distance values and the respective arc distance values relative to the upper occlusal plane 702 associated with the upper teeth 13, in additional non-limiting embodiments of the present technology (not depicted), the processor 550 may be configured to determine the respective distances between the points of the first portion 610 and the second portion 611 relative to respective individual occlusal planes associated with the upper teeth 13. For example, the processor 550 may be configured to determine a given one of the respective orthogonal distance value 708 and the respective arc distance value 710 from the given point 706 associated with the given lower tooth 16 to a respective individual occlusal plane (not depicted) associated with the given upper tooth 17. To that end, the processor 550 may be configured to determine the respective individual occlusal plane (not depicted) associated with the given upper tooth 17 based on a respective upper tooth 3D representation 607 thereof as a plane extending through cusps of the given upper tooth 17, as an example. As may become apparent, in these embodiments, the processor 550 may be configured to determine the respective orthogonal distance values along normal vectors associated with the respective individual occlusal planes of the upper teeth 13.

Further, based on the so determined respective distance values between each point of the first portion 610 and the second portion 611, the processor 550 may be configured to determine the set of occlusal points indicative of the occlusal contacts between the lower teeth 12 and the upper teeth 13.

In accordance with some non-limiting embodiments of the present technology, the processor 550 may be configured to determine the set of occlusal points by filtering out those points of the first portion 611 that are less indicative of the occlusal contacts between the lower teeth 12 and the upper teeth 13. In this regard, in some non-limiting embodiments of the present technology, the processor 550 may be configured to generate a voxel grid 712 around the first portion 610.

How the processor 550 can be configured to determine points more indicative of the occlusal contacts using the voxel grid 712 for inclusion thereof in the set of occlusal points, will be described immediately below with referenced to FIGS. 8A and 8B, considering a segment 714 of the voxel grid 712 including the respective tooth 3D representation 606 of the given lower tooth 16, as an example.

Determining the Occlusal Contacts

Figure 8A:
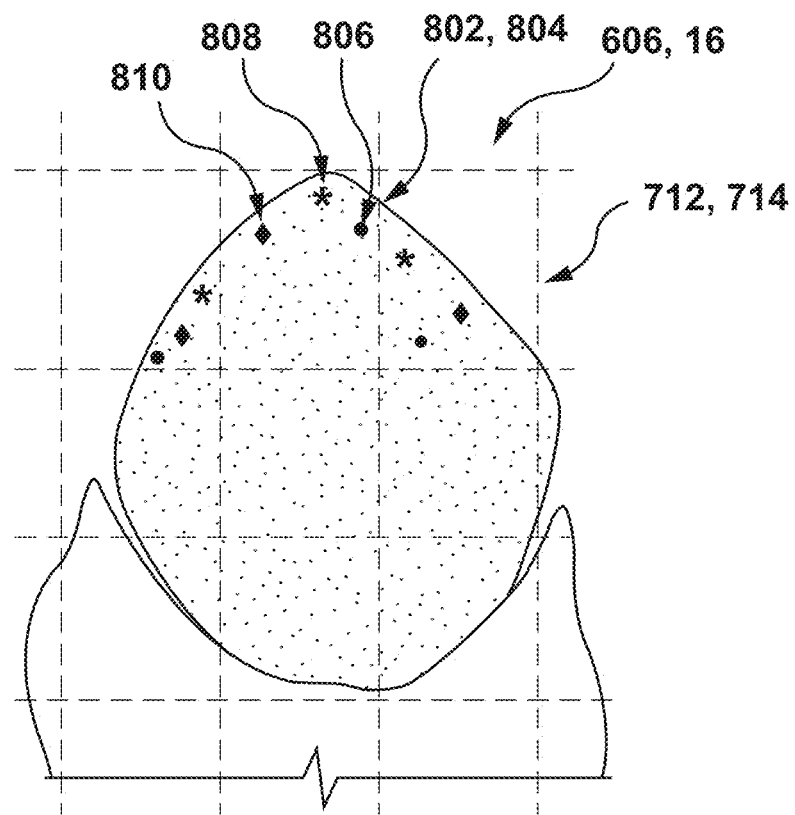
FIGS. 8A and 8B depict lateral and horizontal projections of a respective 3D model of a given one of the subject's teeth present in FIG. 1 illustrating a step for determining, by the processor of FIG. 5, a set of points representative of the occlusal contacts, according to certain embodiments of the present technology.
Figure 8B:
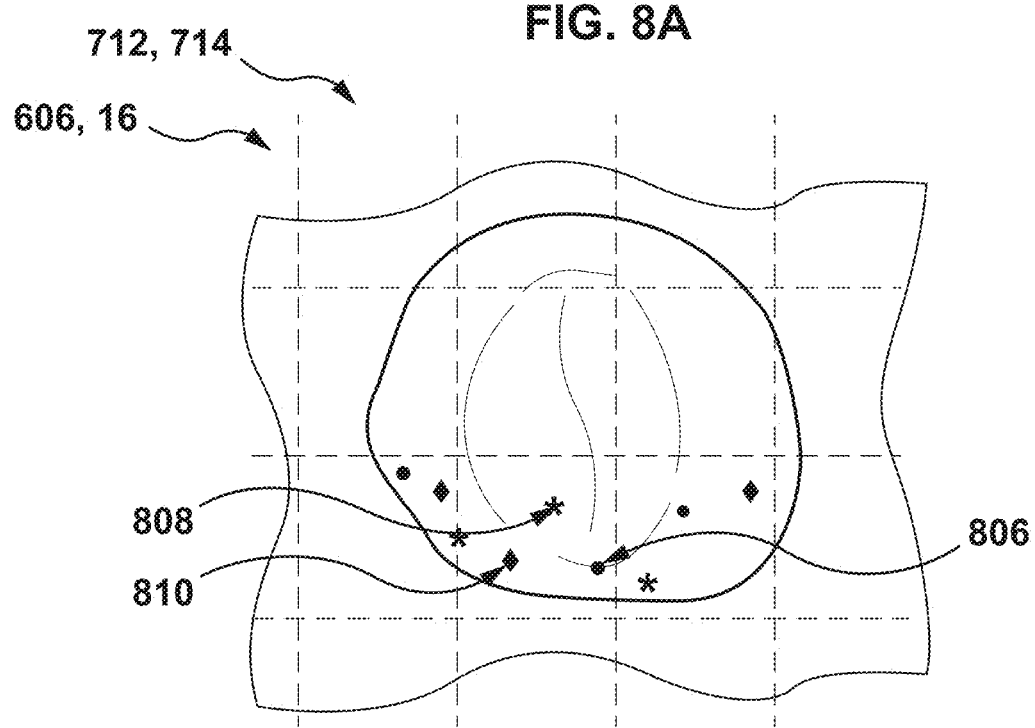

With reference to FIGS. 8A and 8B, there are depicted lateral and horizontal projections of the segment 714 including points of the respective tooth 3D representation 606 of the given lower tooth 16 illustrating a step for determining, by the processor 550, the set of occlusal points, in accordance with certain non-limiting embodiments of the present technology.

As it can be appreciated, each voxel of the voxel grid 712 contains a respective set of points of the first portion 610—such as a given voxel 802 associated with the respective tooth 3D representation 606 containing a respective set of points 804 thereof. Thus, by identifying, in the respective set of points 804, and removing therefrom points non-indicative and/or less indicative of the occlusal contacts between the lower teeth 12 and the upper teeth 13, the processor 550 can be configured to determine occlusal points indicative of at least one occlusal contact between the lower teeth 12 and the upper teeth 13 within the given voxel 802—such as that between the given lower tooth 16 and the given upper tooth 17. As noted hereinabove, the processor 550 may be configured to determine the occlusal points in the given voxel 802 based on respective distance values associated with each one of the respective set of points 804.

For example, in some non-limiting embodiments of the present technology, the processor 550 may be configured to determine, in the respective set of points 804, a single occlusal point 806 for inclusion thereof in the set of occlusal points. It should be noted that it is not limited how the processor 550 may be configured to determine the single occlusal point 806 in the respective set of points 804 of the given voxel 802 indicative of the at least one occlusal contact between the given lower tooth 16 and the upper teeth 13. For example, in those embodiments where the processor 550 is configured to determine the respective distance values between the points of the first portion 610 and the second portion 611 as shortest paths therebetween, based on the signed distance field as described above, the processor 550 may be configured to determine the single occlusal point 806 as being a point of the respective set of points 804 associated with a minimum respective distance value to the second portion 611 within the signed distance field associated therewith.

However, in other non-limiting embodiments of the present technology, the processor 550 may be configured to determine the single occlusal point 806 as being a point of the respective set of points 804 associated with a maximum respective distance value. In yet other non-limiting embodiments of the present technology, the processor 550 may be configured to determine the single occlusal point 806 as being a point associated with an intermediate respective distance value between the minimum respective distance value and the maximum respective distance value, such as a median respective distance value amongst those associated with points of the respective set of points 804, as an example.

Further, instead of determining, in the respective set of points 804, the single occlusal point 806, in additional non-limiting embodiments of the present technology, the processor 550 may be configured to determine, in the respective set of occlusal points 804, a subset of occlusal points (not depicted) based on a predetermined interval of associated respective distance values. For example, the processor 550 may be configured to determine the subset of occlusal points based on the predetermined interval of the associated respective distance values from about 0.50 to about 0.55 mm.

In some non-limiting embodiments of the present technology, to determine the single occlusal point 806 in the respective set of points 804 of the given voxel 802, the processor 550 may be configured to apply a Bounding Volume Hierarchy algorithm.

Further, in those embodiments where the processor 550 is configured to determine the respective distance values between the points of the first portion 610 and the second portion relative to the upper occlusal plane 702, as described above, the processor 550 may be configured to determine, in the respective set of points 804, a single orthogonal occlusal point 808 and a single arc occlusal point 810, based on the respective orthogonal distance values and the respective arc distance values, respectively. In these embodiments, the processor 550 may be configured to determine the single orthogonal occlusal point 808 and the single arc occlusal point 810 similar to determining the single occlusal point 806 as described above. Further, the processor 550 may be configured to include both the single orthogonal occlusal point 808 and the single arc occlusal point 810 in the set of occlusal points.

Additionally, in other non-limiting embodiments of the present technology, instead of determining the single orthogonal occlusal point 808 and the single arc occlusal point 810, the processor 550 may be configured to determine, in the respective set of points 804, a subset of orthogonal occlusal points and a subset of arc occlusal points (both not depicted), respectively, by applying a similar approach as described above with respect to the subset of occlusal points (not depicted).

It should be expressly understood that the single occlusal point 806, the single orthogonal occlusal point 808, and the single arc occlusal point 810 are depicted in FIGS. 8A and 8B as different points of the respective set of points 804 solely for purposes of clarity of explanation of the present technology, and in some non-limiting embodiments of the present technology, at least some of them may coincide.

Thus, by applying one of the approaches described above to each voxel of the voxel grid 712, the processor 550 may be configured to determine the set of occlusal points indicative of the occlusal contacts between the lower teeth 12 and the upper teeth 13 of the subject.

Further, as alluded to above, in some non-limiting embodiments of the present technology, the processor 550 may be configured, based on the set of occlusal points, model the movements of the lower teeth 12 relative to the upper teeth 13 to determine (or otherwise revise already a determined one) the orthodontic treatment for the subject.

In specific non-limiting embodiments of the present technology, to determine the orthodontic treatment, the processor 550 may be configured to apply one or more approaches described in a co-owned U.S. Pat. No. 10,993,782-B1, issued on May 4, 2021 and entitled "SYSTEMS AND METHODS FOR DETERMINING A TOOTH TRAJECTORY," the content of which is incorporated herein by reference in its entirety.

Figure 9:
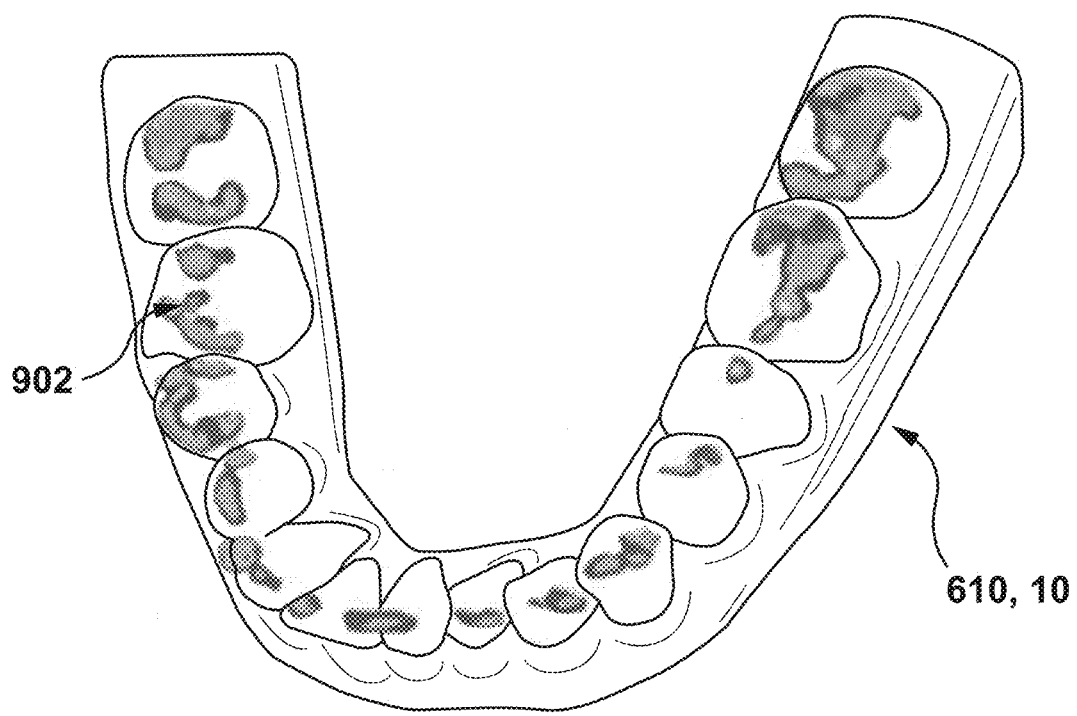
FIG. 9 depicts a schematic diagram of an example depth map representation generated, by the processor of FIG. 5, to visualize the set of occlusal points on the 3D model of FIG. 6, according to certain non-limiting embodiments of the present technology.

Further, in additional non-limiting embodiments of the present technology, the processor 550 may be configured to display the set of occlusal points indicative of the occlusal contacts between the lower teeth 12 and the upper teeth 13 by mapping respective distance values associated with each one of the set of occlusal points on at least one of the first portion 610 and the second portion 611 to generate a depth map representation 902 of the occlusal contacts, which is schematically depicted in FIG. 9, in accordance with certain non-limiting embodiments of the present technology.

In some non-limiting embodiments of the present technology, the depth map representation 902 may be a monochromatic depth map representation where greater values of the respective distance values associated with the set of occlusal points of the first portion 610 are assigned greater intensity values of a given color, and vice versa. In other non-limiting embodiments of the present technology, the depth map representation 902 may be a polychromatic heat map representation associated with a predetermined color spectrum including at least two colors. In this example, the greater values of the respective distance values are assigned respective colors closer to a lower boundary of the predetermined color spectrum (being a green color, for example), and smaller values of the respective distance values are assigned colors closer a higher boundary (being a red color, for example) of the predetermined color spectrum.

In additional non-limiting embodiments of the present technology, the processor 550 may be configured to store the depth map representation 902 in one of the solid-state drive 560 and the random-access memory 570 for further causing display thereof on a display, such as the screen 422. The depth map representation 902 may be displayed on the screen 422, for example, for examining the occlusal contacts between the lower teeth 12 and the upper teeth 13 by the practicing clinician, who may further manually amend the orthodontic treatment determined as described above based on her/his expertise.

Method

Figure 10:
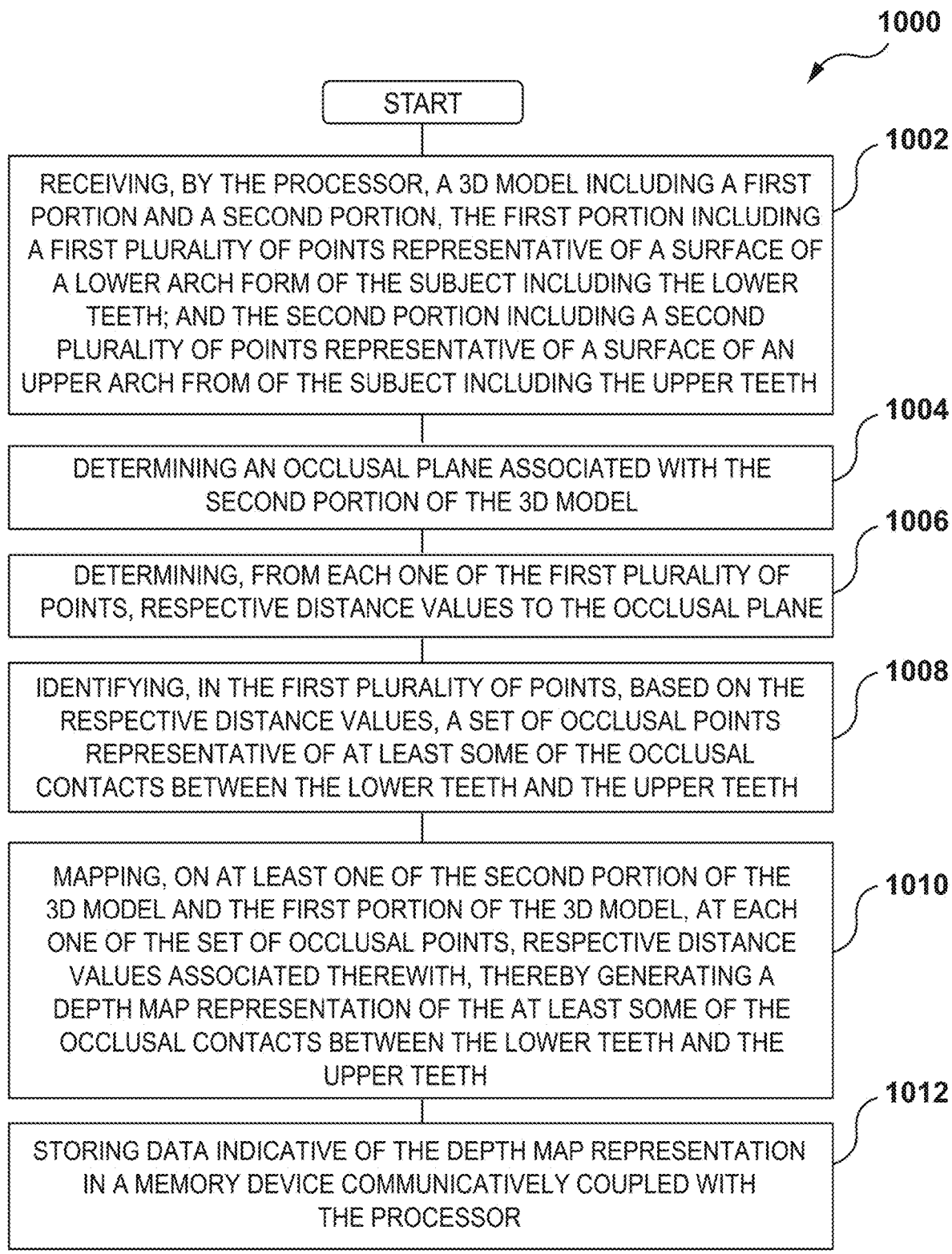
FIG. 10 depicts a flowchart of a method of determining the occlusal contacts between the subject's teeth present in FIG. 1, according to certain embodiments of the present technology.

Given the architecture and the examples provided hereinabove, it is possible to execute a method for determining the occlusal contacts between the lower teeth 12 and the upper teeth 13 of the subject. With reference now to FIG. 10, there is depicted a flowchart of a method 1000, according to certain non-limiting embodiments of the present technology. The method 1000 may be executed by the processor 550 of the system 400.

Step 1002: Receiving, by the Processor, a 3D Model Including a First Portion and a Second Portion, the First Portion Including a First Plurality of Points Representative of a Surface of a Lower Arch Form of the Subject Including the Lower Teeth; and the Second Portion Including a Second Plurality of Points Representative of a Surface of an Upper Arch from of the Subject Including the Upper Teeth The method 1000 commences at step 1002 with the processor 550 being configured to receive the image data of the lower teeth 12 and the upper teeth 13. To that end, in some non-limiting embodiments of the present technology, the processor 550 may be configured to receive point cloud 3D representations of the subject's teeth—such as the 3D model 600 including the first portion 610 and the second portion 611 including points respectively representative of each one of the lower arch from 10 and the upper arch from 11, as described above with reference to FIG. 6.

In additional non-limiting embodiments of the present technology, the processor 550 may further be configured to identify, in the first portion 610, the lower gingiva 3D representation indicative of the lower gingiva 14 and remove the so identified lower gingiva 3D representation from the first portion 610 of the 3D model 600, thereby omitting points thereof from further processing.

The method 1000 thus proceeds to step 1004.

Step 1004: Determining an Occlusal Plane Associated with the Second Portion of the 3D Model Further, at step 1004, the processor 550 may be configured to determine, based on the second portion 611, an occlusal plane associated with the upper teeth 13—such as the upper occlusal plane 702 depicted in FIG. 7.

In some non-limiting embodiments of the present technology, the processor 550 may be configured to determine the upper occlusal plane 702 as a plane extending through incisal edges of incisors (not separately labelled) and cusps of occluding surfaces of posterior ones (not separately labelled) of the upper teeth 13. In other non-limiting embodiments of the present technology, the upper occlusal plane 702 associated with the upper teeth 13 may be predetermined by the practicing clinician, using, a specific articulator, as an example. It should be expressly understood that other techniques to determining the upper occlusal plane 702 associated with the upper teeth 13 may also be used without departing from the scope of the present technology.

In other non-limiting embodiments of the present technology, as further described with reference to FIG. 7, instead of determining the upper occlusal plane 702 associated with the upper teeth 13 as a whole, the processor 550 may be configured to determine individual respective individual occlusal planes associated with each one of the upper teeth 13. For example, the processor 550 may be configured to determine the respective individual occlusal plane (not depicted) associated with the given upper tooth 17, based on the respective upper tooth 3D representation 607, thereof as a plane extending through cusps of the given upper tooth 17.

The method 1000 thus proceeds to step 1006.

Step 1006: Determining, from Each One of the First Plurality of Points, Respective Distance Values to the Occlusal Plane Further, at step 1006, according to certain non-limiting embodiments of the present technology, the processor 550 may be configured to determine the respective distance values between each point of the first portion 610, such as the given point 706, to the second portion 611. The respective distance values can further be used to determine the occlusal contacts between the lower teeth 12 and the upper teeth 13.

To that end, in some non-limiting embodiments of the present technology, the processor 550 may be configured, based on the 3D model 600, to determine the bite position between the lower teeth 12 and the upper teeth 13, as described above with reference to FIG. 6.

Further, in some non-limiting embodiments of the present technology, as described above with reference to FIG. 7, the processor 550 may be configured to determine, based on the bite position, the respective distance values based on the signed distance field associated with the second portion 611. In these embodiments, the processor 550 may be configured to determine the respective distance values as being shortest respective paths between each point of the first portion 610, such as the given point 706, and the second portion 611.

However, as further described above with reference to FIG. 7, in other non-limiting embodiments of the present technology, the processor 550 may be configured to determine the respective distance values as distances between each point of the first portion 610 and the upper occlusal plane 702 associated with the upper teeth 13 determined in step 1006. Further, in these embodiments, the processor 550 may be configured to determine the respective distance values including (1) the respective orthogonal distance values, such as the respective orthogonal distance 708 determined from the given point 706 of the first portion 610 to the upper occlusal plane 702 along the occlusal plane normal vector 704; and (2) the respective arc distance values, such as the respective arc distance value 710 determined from the given point 706 to the upper occlusal plane 702 along the rotational trajectory of the lower arch from 10 relative to the upper arch form 11. As further described above with reference to FIG. 7, in some non-limiting embodiments of the present technology, the processor 550 may be configured to determine the rotational trajectory based on the data of at least one mandibular condyle of the lower arch form 10.

As it may become apparent, in those embodiments where instead of the upper occlusal plane 702, respective individual occlusal planes associated with each one of the upper teeth 13 are used, the processor 550 may be configured to determine the respective orthogonal distance values and the respective arc distance values as distances between the points of the first portion 610 to the respective individual occlusal planes associated with the upper teeth 13. For example, in these embodiments, the processor 550 may be configured to determine (1) the respective orthogonal distance 708, along the respective normal vector associated with the respective individual occlusal plane associated with the given upper tooth 17; and (2) the respective arc distance 710 from the given point 706 relative to the respective individual occlusal plane along the rotational trajectory determined above.

The method 1000 hence advances to step 1008.

Step 1008: Identifying, in the First Plurality of Points, Based on the Respective Distance Values, a Set of Occlusal Points Representative of at Least Some of the Occlusal Contacts Between the Lower Teeth and the Upper Teeth Further, at step 1008, in accordance with certain non-limiting embodiments of the present technology, the processor 550 may be configured, based on the so determined respective distance values, the set of occlusal points of the first portion 610, the set of occlusal point being indicative of the occlusal contacts between the lower teeth 12 and the upper teeth 13.

To that end, as further described above with reference to FIG. 7, the processor 550 may be configured to generate the voxel grid 712 around the first portion 610 of the 3D model 600, and filtering out, from each voxel of the voxel grid 712, points non-indicative and/or less indicative of the occlusal contacts between the lower teeth 12 and the upper teeth 13, the processor 550 may be configured to identify, in the first portion 610, the set of occlusal points.

Considering the example described above with reference to FIGS. 8A and 8B, in the given voxel 802 of the voxel grid 712, the processor 550 may be configured to determine, within the respective set of points 804, at least one of the single occlusal point 806, the single orthogonal occlusal point 808, and the single arc occlusal point 810 indicative of the at least one occlusal contact between the given tooth 16 and the upper teeth 13.

In some non-limiting embodiments of the present technology, the processor 550 may be configured to determine a given one of these single points, such as the single occlusal point 806, as being one of the respective set of points 804 associated with the minimum respective distance value thereamong. However, as further noted above, in other non-limiting embodiments of the present technology, the processor 550 may be configured to determine the single occlusal point 806 as being one of the respective set of points 804 associated with the maximum respective distance value thereamong. In yet further non-limiting embodiments of the present technology, the processor 550 may be configured to determine the single occlusal point 806 as being one of the respective set of points 804 associated with an intermediate respective distance value between the minimum respective distance value and the maximum respective distance value, such as the median respective distance value.

In some non-limiting embodiments of the present technology, the processor may be configured to determine the at least one of the single occlusal point 806, the single orthogonal occlusal point 808, and the single arc occlusal point 810 applying the Bounding Volume Hierarchy algorithm to given voxel 802 of the voxel grid 712.

As described above, in yet other non-limiting embodiments of the present technology, instead of determining at least one of the single occlusal point 806, the single orthogonal occlusal point 808, and the single arc occlusal point 810, the processor 550 may be configured to determine a respective subset of occlusal points based on a respective predetermined interval of respective distance values.

Thus, the processor 550 may be configured to determine, within points of the first portion 610 of the 3D model 600, the set of occlusal points representative of the occlusal contacts between the lower teeth 12 and the upper teeth 13.

Further, in some non-limiting embodiments of the present technology, the processor 550 may be configured, based on the set of occlusal points, model the movements of the lower teeth 12 relative to the upper teeth 13 to determine (or otherwise verify already a determined one) the orthodontic treatment for the subject, as described above.

The method 1000 hence advances to step 1010.

Step 1010: Mapping, on at Least One of the Second Portion of the 3D Model and the First Portion of the 3D Model, at Each One of the Set of Occlusal Points, Respective Distance Values Associated Therewith, Thereby Generating a Depth Map Representation of the at Least Some of the Occlusal Contacts Between the Lower Teeth and the Upper Teeth Further, at step 1010, in some non-limiting embodiments of the present technology, the processor 550 may be configured to display the set of occlusal points indicative of the occlusal contacts between the lower teeth 12 and the upper teeth 13 by mapping respective distance values associated with each one of the set of occlusal points on at least one of the first portion 610 and the second portion 611 to generate the depth map representation 902, as described above with reference to FIG. 9.

The method 1000 thus proceeds to step 1012.

Step 1012: Storing Data Indicative of the Depth Map Representation in a Memory Device Communicatively Coupled with the Processor Finally, at step 1012, in some non-limiting embodiments of the present technology, the processor 550 may be configured to store the depth map representation 902 in one of the solid-state drive 560 and the random-access memory 570 for further causing display thereof on a display, such as the screen 422. As further described above, the depth map representation 902 may be displayed on the screen 422, for example, for examining the occlusal contacts between the lower teeth 12 and the upper teeth 13 by the practicing clinician, who may further manually amend the orthodontic treatment determined as described above based on her/his expertise.

Thus, certain embodiments of the method 1000 may allow identifying and removing, within the points of the first portion 610 representative of the lower arch form 10 of the subject, those points that may be less indicative of the occlusal contacts between the lower teeth 12 and the upper teeth 13, thereby determining the set of occlusal contacts that may further be used for a more efficient modelling of the movements of the lower teeth 12 relative to the upper teeth 13 allowing for saving computational resources of the processor 550 on such modelling.

The method 1000 thus terminates.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method of determining occlusal contacts between lower teeth and upper teeth of a subject, the method comprising:
receiving a 3D model including a first plurality of points representative of a surface of the lower teeth and a second plurality of points representative of a surface of the upper teeth of the subject;
determining, based on the 3D model, a distance field associated with the upper teeth;
determining, based on the distance field, from each one of the first plurality of points, respective distance values to the surface of the upper teeth;
identifying, within the first plurality of points, based on the respective distance values, a set of occlusal points representative of at least some of the occlusal contacts between the lower teeth and the upper teeth;
mapping, on at least one of the lower teeth and the upper teeth in the 3D model, at each one of the set of occlusal points, respective distance values associated therewith, thereby generating a depth map representation of the at least some of the occlusal contacts between the lower teeth and the upper teeth;
storing data indicative of the depth map representation.

2. The method of claim 1, wherein the identifying the set of occlusal points comprises:
generating, in the 3D model, a voxel grid around the first plurality of points of the lower teeth,
each voxel of the voxel grid including a respective set of points of the first plurality of points; and
determining, in a given set of points, a single point representative of an occlusal contact between the lower teeth and the upper teeth within a respective voxel of the voxel grid.

3. The method of claim 2, wherein the determining the single point comprises determining a point with a minimum respective distance value in the respective voxel of the voxel grid of around the first plurality of points.

4. The method of claim 3, wherein the determining the single point further comprises applying a Bounding Volume Hierarchy algorithm to the respective voxel of the voxel grid.

5. The method of claim 1, wherein the determining the respective distance values further comprises:
determining, based on the 3D model, an occlusal plane associated with the upper teeth;
determining, from each one of the first plurality of points, along a respective normal vector to the occlusal plane, respective orthogonal distance values;
determining, from each one of the first plurality of points, based on the 3D model, along a predetermined rotational trajectory of the lower teeth relative to the upper teeth to the occlusal plane, respective arc distance values.

6. The method of claim 5, further comprising determining, in the 3D model, the predetermined rotational trajectory of the lower teeth relative to the upper teeth based on data of at least one mandibular condyle of the subject.

7. The method of claim 6, wherein the determining the predetermined rotational trajectory comprises determining, in the 3D model, based on the data of the at least one mandibular condyle, a rotation center of the lower teeth relative to the upper teeth.

8. The method of claim 7, wherein the determining the predetermined rotational trajectory further comprises determining, based on the 3D model, a bite position between the lower teeth and the upper teeth.

9. The method of claim 5, wherein the identifying the set of occlusal points further comprises:
determining, based on the respective orthogonal distance values, an orthogonal subset of occlusal points;
determining, based on the respective arc distance values, an arc subset of occlusal points; and
merging the orthogonal subset of occlusal points and the arc subset of occlusal points.

10. The method of claim 1, wherein the first plurality of points includes points representative of a lower gingiva associated with the lower teeth, and the method further comprises, prior to the determining the respective distance values:
identifying, within the first plurality of points, the points representative of the lower gingiva; and
removing, from the first plurality of points, the points representative of the lower gingiva from further consideration.

11. The method of claim 1, further comprising causing display of the depth map representation on the at least one of the lower teeth and the upper teeth in the 3D model.

12. The method of claim 1, wherein the depth map representation is for determining an orthodontic treatment for the subject.

13. A system for determining occlusal contacts between lower teeth and upper teeth of a subject, the system comprising an electronic device including:
one or more processors;
a non-transitory memory device storing instructions, which, when executed by the one or more processors, cause the system to:
receive a 3D model including a first plurality of points representative of a surface of the lower teeth and a second plurality of points representative of a surface of the upper teeth of the subject;

determine, based on the 3D model, a distance field associated with the upper teeth;

determine, in the 3D model, based on the distance field, from each one of the first plurality of points, respective distance values to the surface of the upper teeth;

identify, within the first plurality of points, based on the respective distance values, a set of occlusal points representative of at least some of the occlusal contacts between the lower teeth and the upper teeth;

map, on at least one of the lower teeth and the upper teeth in the 3D model, at each one of the set of occlusal points, respective distance values associated therewith, thereby generating a depth map representation of the at least some of the occlusal contacts between the lower teeth and the upper teeth;

store data indicative of the depth map representation in a memory device communicatively coupled with the one or more processors.

14. The system of claim 13, wherein to identify the set of occlusal points within the first plurality of points, the instructions cause the system to:

generate, in the 3D model, a voxel grid around the first plurality of points of the lower teeth, each voxel of the voxel grid including a respective set of points of the first plurality of points; and determine, in a given set of points, a single point representative of an occlusal contact between the lower teeth and the upper teeth within a respective voxel of the voxel grid.

15. The system of claim 14, wherein the instructions cause the system to determine the single point as being a point with a minimum respective distance value in the respective voxel of the voxel grid around the first plurality of points.

16. The system of claim 15, wherein to determine the single point, the instructions cause the system to apply a Bounding Volume Hierarchy algorithm to the respective voxel of the voxel grid.

17. The system of claim 13, wherein to determine the respective distance values, the instructions further cause the system to:

determine, in the 3D model, an occlusal plane associated with the upper teeth;

determine, from each one of the first plurality of points, along a respective normal vector to the occlusal plane, respective orthogonal distance values;

determine, from each one of the first plurality of points, along a predetermined rotational trajectory of the lower teeth relative to the upper teeth of the 3D model to the occlusal plane, respective arc distance values.

18. The system of claim 17, wherein to identify the set of occlusal points, the instructions further cause the system to:

determine, based on the respective orthogonal distance values, an orthogonal subset of occlusal points;

determine, based on the respective arc distance values, an arc subset of occlusal points; and merge the orthogonal subset of occlusal points and the arc subset of occlusal points.

19. The system of claim 13, wherein the first plurality of points includes points representative of a lower gingiva associated with the lower teeth, and the instructions further cause the system to, prior to determining the respective distance values:

identify, within the first plurality of points, points representative of the lower gingiva; and remove, from the first plurality of points, the points representative of the lower gingiva from further consideration.

20. The system of claim 13, wherein the instructions further cause the system to cause display of the depth map representation on the at least one of the lower teeth and the upper teeth in the 3D model.

* * * * *